United States Patent [19]
Hannah et al.

[11] Patent Number: 5,872,216
[45] Date of Patent: Feb. 16, 1999

[54] MATERIALS AND METHODS FOR INCREASING CORN SEED WEIGHT

[75] Inventors: L. Curtis Hannah, Gainesville, Fla.; Michael Giroux, Pullman, Wash.

[73] Assignee: University of Florida Research Foundation, Inc., Gainesville, Fla.

[21] Appl. No.: 874,162

[22] Filed: Jun. 13, 1997

Related U.S. Application Data

[60] Division of Ser. No. 485,241, Jun. 7, 1995, Pat. No. 5,650, 557, which is a continuation-in-part of Ser. No. 299,675, Sep. 1, 1994, Pat. No. 5,589,618.

[51] Int. Cl.⁶ ........................... C12N 15/05; C12N 15/11; A01H 5/00; C07K 14/415
[52] U.S. Cl. ........................... 530/376; 530/350; 530/370; 800/205; 800/208; 536/23.1; 536/23.2; 536/23.6; 435/172.3; 435/172.1; 935/9; 935/10
[58] Field of Search ..................................... 800/205, 208; 530/350, 370; 536/23.1, 23.2, 23.6; 435/172.3, 172.1; 935/9, 10

*Primary Examiner*—Ponnathapura Achutamurthy
*Assistant Examiner*—Phuong T. Bui
*Attorney, Agent, or Firm*—Saliwanchik, Lloyd & Saliwanchik

[57] ABSTRACT

The subject invention pertains to novel variants of the maize gene, Shrunken2 (Sh2) and a method of using that gene. The variant gene, Sh2-m1Rev6, encodes a subunit of the ADP-glucose pyrophosphorylase (AGP) enzyme that has additional amino acids inserted in or near the allosteric binding site of the protein. Corn seed expressing the Sh2-m1Rev6 gene has a 15% weight increase over wild type seed. The increase in seed weight is not associated simply with an increase in percentage starch content of the seed.

6 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 7745 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TAAGAGGGGT  GCACCTAGCA  TAGATTTTTT  GGGCTCCCTG  GCCTCTCCTT  TCTTCCGCCT    60
GAAAACAACC  TACATGGATA  CATCTGCAAC  CAGAGGGAGT  ATCTGATGCT  TTTTCCTGGG   120
CAGGGAGAGC  TATGAGACGT  ATGTCCTCAA  AGCCACTTTG  CATTGTGTGA  AACCAATATC   180
GATCTTTGTT  ACTTCATCAT  GCATGAACAT  TTGTGGAAAC  TACTAGCTTA  CAAGCATTAG   240
TGACAGCTCA  GAAAAAGTT   ATCTCTGAAA  GGTTTCATGT  GTACCGTGGG  AAATGAGAAA   300
TGTTGCCAAC  TCAAACACCT  TCAATATGTT  GTTTGCAGGC  AAACTCTTCT  GGAAGAAAGG   360
TGTCTAAAAC  TATGAACGGG  TTACAGAAAG  GTATAAACCA  CGGCTGTGCA  TTTTGGAAGT   420
ATCATCTATA  GATGTCTGTT  GAGGGGAAAG  CCGTACGCCA  ACGTTATTTA  CTCAGAAACA   480
GCTTCAACAC  ACAGTTGTCT  GCTTTATGAT  GGCATCTCCA  CCCAGGCACC  CACCATCACC   540
TATTCACCTA  TCTCTCGTGC  CTGTTTATTT  TCTTGCCCTT  TCTGATCATA  AAAATCATT    600
AAGAGTTTGC  AAACATGCAT  AGGCATATCA  ATATGCTCAT  TTATTAATTT  GCTAGCAGAT   660
CATCTTCCTA  CTCTTTACTT  TATTTATTGT  TTGAAAAATA  TGTCCTGCAC  CTAGGGAGCT   720
CGTATACAGT  ACCAATGCAT  CTTCATTAAA  TGTGAATTTC  AGAAAGGAAG  TAGGAACCTA   780
TGAGAGTATT  TTTCAAAATT  AATTAGCGGC  TTCTATTATG  TTTATAGCAA  AGGCCAAGGG   840
CAAAATCGGA  ACACTAATGA  TGGTTGGTTG  CATGAGTCTG  TCGATTACTT  GCAAGAAATG   900
TGAACCTTTG  TTTCTGTGCG  TGGGCATAAA  ACAAACAGCT  TCTAGCCTCT  TTTACGGTAC   960
TTGCACTTGC  AAGAAATGTG  AACTCCTTTT  CATTTCTGTA  TGTGGACATA  ATGCCAAAGC  1020
ATCCAGGCTT  TTTCATGGTT  GTTGATGTCT  TTACACAGTT  CATCTCCACC  AGTATGCCCT  1080
CCTCATACTC  TATATAAACA  CATCAACAGC  ATCGCAATTA  GCCACAAGAT  CACTTCGGGA  1140
GGCAAGTGTG  ATTTCGACCT  TGCAGCCACC  TTTTTTTGTT  CTGTTGTAAG  TATACTTTCC  1200
CTTACCATCT  TTATCTGTTA  GTTTAATTTG  TAATTGGGAA  GTATTAGTGG  AAAGAGGATG  1260
AGATGCTATC  ATCTATGTAC  TCTGCAAATG  CATCTGACGT  TATATGGGCT  GCTTCATATA  1320
ATTTGAATTG  CTCCATTCTT  GCCGACAATA  TATTGCAAGG  TATATGCCTA  GTTCCATCAA  1380
```

| | | | | | | |
|---|---|---|---|---|---|---|
| AAGTTCTGTT | TTTTCATTCT | AAAAGCATTT | TAGTGGCACG | CAATTTTGTC | CATGAGGGAA | 1440 |
| AGGAAATCTG | TTTTGGTTAC | TTTGCTTGAG | GTGCATTCTT | CATATGTCCA | GTTTTATGGA | 1500 |
| AGTAATAAAC | TTCAGTTTGG | TCATAAGATG | TCATATTAAA | GGGCAAACAT | ATATTCAATG | 1560 |
| TTCAATTCAT | CGTAAATGTT | CCCTTTTTGT | AAAAGATTGC | ATACTCATTT | ATTTGAGTTG | 1620 |
| CAGGTGTATC | TAGTAGTTGG | AGGAGATATG | CAGTTTGCAC | TTGCATTGGA | CACGAACTCA | 1680 |
| GGTCCTCACC | AGATAAGATC | TTGTGAGGGT | GATGGGATTG | ACAGGTTGGA | AAAATTAAGT | 1740 |
| ATTGGGGGCA | GAAAGCAGGA | GAAAGCTTTG | AGAAATAGGT | GCTTGGTGG | TAGAGTTGCT | 1800 |
| GCAACTACAC | AATGTATTCT | TACCTCAGAT | GCTTGTCCTG | AAACTCTTGT | AAGTATCCAC | 1860 |
| CTCAATTATT | ACTCTTACAT | GTTGGTTTAC | TTTACGTTTG | TCTTTTCAAG | GGAAATTTAC | 1920 |
| TGTATTTTTT | GTGTTTTGTG | GGAGTTCTAT | ACTTCTGTTG | GACTGGTTAT | TGTAAAGATT | 1980 |
| TGTTCAAATA | GGGTCATCTA | ATAATTGTTT | GAAATCTGGG | AACTGTGGTT | TCACTGCGTT | 2040 |
| CAGGAAAAAG | TGAATTATTG | GTTACTGCAT | GAATAACTTA | TGGAAATAGA | CCTTAGAGTT | 2100 |
| GCTGCATGAT | TATCACAAAT | CATTGCTACG | ATATCTTATA | ATAGTTCTTT | CGACCTCGCA | 2160 |
| TTACATATAT | AACTGCAACT | CCTAGTTGCG | TTCAAAAAAA | AAAATGCAAC | TCTTAGAACG | 2220 |
| CTCACCAGTG | TAATCTTTCC | TGAATTGTTA | TTTAATGGCA | TGTATGCACT | ACTTGTATAC | 2280 |
| TTATCTAGGA | TTAAGTAATC | TAACTCTAGG | CCCCATATTT | GCAGCATTCT | CAAACACAGT | 2340 |
| CCTCTAGGAA | AAATTATGCT | GATGCAAACC | GTGTATCTGC | TATCATTTG | GGCGGAGGCA | 2400 |
| CTGGATCTCA | GCTCTTTCCT | CTGACAAGCA | CAAGAGCTAC | GCCTGCTGTA | AGGGATAACA | 2460 |
| CTGAACATCC | AACGTTGATT | ACTCTATTAT | AGTATTATAC | AGACTGTACT | TTTCGAATTT | 2520 |
| ATCTTAGTTT | TCTACAATAT | TTAGTGGATT | CTTCTCATTT | TCAAGATACA | CAATTGATCC | 2580 |
| ATAATCGAAG | TGGTATGTAA | GACAGTGAGT | TAAAAGATTA | TATTTTTTGG | GAGACTTCCA | 2640 |
| GTCAAATTTT | CTTAGAAGTT | TTTTGGTCC | AGATGTTCAT | AAAGTCGCCG | CTTTCATACT | 2700 |
| TTTTTTAATT | TTTTAATTGG | TGCACTATTA | GGTACCTGTT | GGAGGATGTT | ACAGGCTTAT | 2760 |
| TGATATCCCT | ATGAGTAACT | GCTTCAACAG | TGGTATAAAT | AAGATATTTG | TGATGAGTCA | 2820 |
| GTTCAATTCT | ACTTCGCTTA | ACCGCCATAT | TCATCGTACA | TACCTTGAAG | GCGGGATCAA | 2880 |
| CTTTGCTGAT | GGATCTGTAC | AGGTGATTTA | CCTCATCTTG | TTGATGTGTA | ATACTGTAAT | 2940 |
| TAGGAGTAGA | TTTGTGTGGA | GAGAATAATA | AACAGATGCC | GAGATTCTTT | TCTAAAAGTC | 3000 |
| TAGATCCAAA | GGCATTGTGG | TTCAAAACAC | TATGGACTTC | TACCATTTAT | GTCATTACTT | 3060 |
| TGCCTTAATG | TTCCATTGAA | TGGGGCAAAT | TATTGATTCT | ACAAGTGTTT | AATTAAAAAC | 3120 |
| TAATTGTTCA | TCCTGCAGGT | ATTAGCGGCT | ACACAAATGC | CTGAAGAGCC | AGCTGGATGG | 3180 |
| TTCCAGGGTA | CAGCAGACTC | TATCAGAAAA | TTTATCTGGG | TACTCGAGGT | AGTTGATATT | 3240 |
| TTCTCGTTTA | TGAATGTCCA | TTCACTCATT | CCTGTAGCAT | TGTTTCTTTG | TAATTTTGAG | 3300 |
| TTCTCCTGTA | TTTCTTTAGG | ATTATTACAG | TCACAAATCC | ATTGACAACA | TTGTAATCTT | 3360 |
| GAGTGGCGAT | CAGCTTATC | GGATGAATTA | CATGGAACTT | GTGCAGGTAT | GGTGTTCTCT | 3420 |
| TGTTCCTCAT | GTTTCACGTA | ATGTCCTGAT | TTTGGATTAA | CCAACTACTT | TTGGCATGCA | 3480 |
| TTATTTCCAG | AAACATGTCG | AGGACGATGC | TGATATCACT | ATATCATGTG | CTCCTGTTGA | 3540 |
| TGAGAGGTAA | TCAGTTGTTT | ATATCATCCT | AATATGAATA | TGTCATCTTG | TTATCCAACA | 3600 |
| CAGGATGCAT | ATGGTCTAAT | CTGCTTTCCT | TTTTTTTCCC | TTCGGAAGCC | GAGCTTCTAA | 3660 |
| AAATGGGCTA | GTGAAGATTG | ATCATACTGG | ACGTGTACTT | CAATTCTTTG | AAAAACCAAA | 3720 |
| GGGTGCTGAT | TTGAATTCTA | TGGTTAGAAA | TTCCTTGTGT | AATCCAATTC | TTTTGTTTTC | 3780 |

```
CTTTCTTTCT  TGAGATGAAC  CCCTCTTTTA  GTTATTTCCA  TGGATAACCT  GTACTTGACT    3840
TATTCAGAAA  TGATTTTCTA  TTTTGCTGTA  GAATCTGACA  CTAAAGCTAA  TAGCACTGAT    3900
GTTGCAGAGA  GTTGAGACCA  ACTTCCTGAG  CTATGCTATA  GATGATGCAC  AGAAATATCC    3960
ATACCTTGCA  TCAATGGGCA  TTTATGTCTT  CAAGAAAGAT  GCACTTTTAG  ACCTTCTCAA    4020
GTAATCACTT  TCCTGTGACT  TATTTCTATC  CAACTCCTAG  TTTACCTTCT  AACAGTGTCA    4080
ATTCTTAGGT  CAAAATATAC  TCAATTACAT  GACTTTGGAT  CTGAAATCCT  CCCAAGAGCT    4140
GTACTAGATC  ATAGTGTGCA  GGTAAGTCTG  ATCTGTCTGG  AGTATGTGTT  CTGTAAACTG    4200
TAAATTCTTC  ATGTCAAAAA  GTTGTTTTTG  TTTCCAGTTT  CCACTACCAA  TGCACGATTT    4260
ATGTATTTC   GCTTCCATGC  ATCATACATA  CTAACAATAC  ATTTACGTA   TTGTGTTAGG    4320
CATGCATTTT  TACGGGCTAT  TGGGAGGATG  TTGGAACAAT  CAAATCATTC  TTTGATGCAA    4380
ACTTGGCCCT  CACTGAGCAG  GTACTCTGTC  ATGTATTCTG  TACTGCATAT  ATATTACCTG    4440
GAATTCAATG  CATAGAATGT  GTTAGACCAT  CTTAGTTCCA  TCCTGTTTTC  TTCAATTAGC    4500
TTATCATTTA  ATAGTTGTTG  GCTAGAATTT  AAACACAAAT  TTACCTAATA  TGTTTCTCTC    4560
TTCAGCCTTC  CAAGTTTGAT  TTTTACGATC  CAAAACACC   TTTCTTCACT  GCACCCCGAT    4620
GCTTGCCTCC  GACGCAATTG  GACAAGTGCA  AGGTATATGT  CTTACTGAGC  ACAATTGTTA    4680
CCTGAGCAAG  ATTTTGTGTA  CTTGACTTGT  TCTCCTCCAC  AGATGAAATA  TGCATTTATC    4740
TCAGATGGTT  GCTTACTGAG  AGAATGCAAC  ATCGAGCATT  CTGTGATTGG  AGTCTGCTCA    4800
CGTGTCAGCT  CTGGATGTGA  ACTCAAGGTA  CATACTCTGC  CAATGTATCT  ACTCTTGAGT    4860
ATACCATTTC  AACACCAAGC  ATCACCAAAT  CACACAGAAC  AATAGCAACA  AAGCCTTTTA    4920
GTTCCAAGCA  ATTTAGGGTA  GCCTAGAGTT  GAAATCTAAC  AAAACAAAAG  TCAAAGCTCT    4980
ATCACGTGGA  TAGTTGTTTT  CCATGCACTC  TTATTTAAGC  TAATTTTTTG  GGTATACTAC    5040
ATCCATTTAA  TTATTGTTTT  ATTGCTTCTT  CCCTTTGCCT  TTCCCCATT   ACTATCGCGT    5100
CTTAAGATCA  TACTACGCAC  TAGTGTCTTT  AGAGGTCTCT  GGTGGACATG  TTCAAACCAT    5160
CTCAATCGGT  GTTGGACAAG  TTTTTCTTGA  ATTTGTGCTA  CACCTAACCT  ATCACGTATG    5220
TCATCGTTTC  AAACTCGATC  CTTCCTGTAT  CATCATAAAT  CCAATGCAAC  ATACGCATTT    5280
ATGCAACATT  TATCTGTTGA  ACATGTCATC  TTTTTGTAGG  TTAACATTAT  GCACCATACA    5340
ATGTAGCATG  TCTAATCATC  ATCCTATAAA  ATTTACATTT  TAGCTTATGT  GGTATCCTCT    5400
TGCCACTTAG  AACACCATAT  GCTTGATGCC  ATTTCATCCA  CCCTGCTTTG  ATTCTATGGC    5460
TAACATCTTC  ATTAATATCC  TCGCCTCTCT  GTATCATTGG  TCCTAAATAT  GGAAATACAT    5520
TCTTTCTGGG  CACTACTTGA  CCTTCCAAAC  TAACGTCTCC  TTTGCTCCTT  TCTTGTGTGT    5580
AGTAGTACCG  AAGTCACATC  TCATATATTC  GGTTTTAGTT  CTACTAAGTC  CCGGGTTCGA    5640
TCCCCCTCAG  GGGTGAATTT  CGGGCTTGGT  AAAAAAAATC  CCCTCGCTGT  GTCCGCCCG    5700
CTCTCGGGGA  TCGATATCCT  GCGCGCCACC  CTCCGGCTGG  GCATTGCAGA  GTGAGCAGTT    5760
GATCGGCTCG  TTAGTGATGG  GGAGCGGGGT  TCAAGGGTTT  TCTCGGCCGG  GACCATGTTT    5820
CGGTCTCTTA  ATATAATGCC  GGGAGGGCAG  TCTTTCCCTC  CCCGGTCGAG  TTTTAGTTCT    5880
ACCGAGTCTA  AAACCTTTGG  ACTCTAGAGT  CCCCTGTCAC  AACTCACAAC  TCTAGTTTTC    5940
TATTTACTTC  TACCTAGCGT  TTATTAATGA  TCACTATATC  GTCTGTAAAA  AGCATACACC    6000
AATGTAATCC  CCTTGTATGT  CCCTTGTAAT  ATTATCCATC  ACAAGAAAAA  AAGGTAAGGC    6060
TCAAAGTTGA  CTTTTGATAT  AGTCCTATTC  TAATCGAGAA  GTCATCTGTA  TCTTCGTCTC    6120
TTGTTCGAAC  ACTAGTCACA  AAATTTTTTG  TACATGTTCT  TAATGAGTCC  AACGTAATAT    6180
```

-continued

| | | | | | | |
|---|---|---|---|---|---|---|
| TCCTTGATAT | TTTGTCATAA | GCCCTCATCA | AGTCAATGAA | AATCACGTGT | AGGTCCTTCA | 6240 |
| TTTGTTCCTT | ATACTGCTCC | ATCACTTGTC | TCATTAAGAA | AATCTCTCTC | ATAGTTAACC | 6300 |
| TTTTGGCATG | AAACAAAATC | ACACAGAAGT | TGTTTCCTTT | TTTTAAGATC | CCACACAAAA | 6360 |
| GAGGTTTGAT | CTAAGGAATC | TGGATCCCTG | ACAGGTTTAT | CAAAATCCTT | TGTGTTTTTC | 6420 |
| TTAAAACTGA | ATATTCCTCC | AGCTTCTAGT | ATTGATGTAA | TATTCAATCT | GTTTAGCAAG | 6480 |
| TGAACACCTT | GGTTCTTGTT | GTTACTGTAC | CCCCCCCCC | CCCCCCCCC | CGAGGCCCAG | 6540 |
| ATTACCACGA | CATGAATACA | AGAATATTGA | ACCCAGATCT | AGAGTTTGTT | TGTACTGTTG | 6600 |
| AAAATCGGTG | ACAATTCATT | TTGTTATTGC | GCTTTCTGAT | AACGACAGGA | CTCCGTGATG | 6660 |
| ATGGGAGCGG | ACACCTATGA | AACTGAAGAA | GAAGCTTCAA | AGCTACTGTT | AGCTGGGAAG | 6720 |
| GTCCCAGTTG | GAATAGGAAG | GAACACAAAG | ATAAGGTGAG | TATGGATGTG | GAACCACCGG | 6780 |
| TTAGTTCCCA | AAAATATCAC | TCACTGATAC | CTGATGGTAT | CCTCTGATTA | TTTTCAGGAA | 6840 |
| CTGTATCATT | GACATGAATG | CTAGGATTGG | GAAGAACGTG | GTGATCACAA | ACAGTAAGGT | 6900 |
| GAGCGAGCGC | ACCTACATGG | GTGCAGAATC | TTGTGTGCTC | ATCTATCCTA | ATTCGGTAAT | 6960 |
| TCCTATCCAG | CGCTAGTCTT | GTGACCATGG | GGCATGGGTT | CGACTCTGTG | ACAGGGCATC | 7020 |
| CAAGAGGCTG | ATCACCCGGA | AGAAGGGTAC | TCGTACTACA | TAAGGTCTGG | AATCGTGGTG | 7080 |
| ATCTTGAAGA | ATGCAACCAT | CAACGATGGG | TCTGTCATAT | AGATCGGCTG | CGTGTGCGTC | 7140 |
| TACAAAACAA | GAACCTACAA | TGGTATTGCA | TCGATGGATC | GTGTAACCTT | GGTATGGTAA | 7200 |
| GAGCCGCTTG | ACAGAAAGTC | GAGCGTTCGG | GCAAGATGCG | TAGTCTGGCA | TGCTGTTCCT | 7260 |
| TGACCATTTG | TGCTGCTAGT | ATGTACTGTT | ATAAGCTGCC | CTAGAAGTTG | CAGCAAACCT | 7320 |
| TTTTATGAAC | CTTTGTATTT | CCATTACCTG | CTTTGGATCA | ACTATATCTG | TCATCCTATA | 7380 |
| TATTACTAAA | TTTTTACGTG | TTTTTCTAAT | TCGGTGCTGC | TTTTGGGATC | TGGCTTCGAT | 7440 |
| GACCGCTCGA | CCCTGGGCCA | TTGGTTCAGC | TCTGTTCCTT | AGAGCAACTC | CAAGGAGTCC | 7500 |
| TAAATTTTGT | ATTAGATACG | AAGGACTTCA | GCCGTGTATG | TCGTCCTCAC | CAAACGCTCT | 7560 |
| TTTTGCATAG | TGCAGGGGTT | GTAGACTTGT | AGCCCTTGTT | TAAAGAGGAA | TTTGAATATC | 7620 |
| AAATTATAAG | TATTAAATAT | ATATTTAATT | AGGTTAACAA | ATTTGGCTCG | TTTTTAGTCT | 7680 |
| TTATTTATGT | AATTAGTTTT | AAAAATAGAC | CTATATTTCA | ATACGAAATA | TCATTAACAT | 7740 |
| CGATA | | | | | | 7745 |

( 2 ) INFORMATION FOR SEQ ID NO:2:

( i ) SEQUENCE CHARACTERISTICS:
        ( A ) LENGTH: 1919 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | | |
|---|---|---|---|---|---|---|
| ACAAGATCAC | TTCGGGAGGC | AAGTGCGATT | TTGATCTTGC | AGCCACCTTT | TTTTGTTCTG | 60 |
| TTGTGTATCT | AGTAGTTGGA | GGAGATATGC | AGTTTGCACT | TGCATTGGAC | ACGAACTCAG | 120 |
| GTCCTCACCA | GATAAGATCT | TGTGAGGGTG | ATGGGATTGA | CAGGTTGGAA | AAATTAAGTA | 180 |
| TTGGGGGCAG | AAAGCAGGAG | AAAGCTTTGA | GAAATAGGTG | CTTTGGTGGT | AGAGTTGCTG | 240 |
| CAACTACACA | ATGTATTCTT | ACCTCAGATG | CTTGTCCTGA | AACTCTTCAT | TCTCAAACAC | 300 |
| AGTCCTCTAG | GAAAAATTAT | GCTGATGCAA | ACCGTGTATC | TGCGATCATT | TTGGGCGGAG | 360 |

| | | | | | |
|---|---|---|---|---|---|
| GCACTGGATC | TCAGCTCTTT | CCTCTGACAA | GCACAAGAGC | TACGCCTGCT | GTACCTGTTG | 420 |
| GAGGATGTTA | CAGGCTTATT | GATATCCCTA | TGAGTAACTG | CTTCAACAGT | GGTATAAATA | 480 |
| AGATATTTGT | GATGAGTCAG | TTCAATTCTA | CTTCGCTTAA | CCGCCATATT | CATCGTACAT | 540 |
| ACCTTGAAGG | CGGGATCAAC | TTTGCTGATG | GATCTGTACA | GGTATTAGCG | GCTACACAAA | 600 |
| TGCCTGAAGA | GCCAGCTGGA | TGGTTCCAGG | GTACAGCAGA | CTCTATCAGA | AAATTTATCT | 660 |
| GGGTACTCGA | GGATTATTAC | AGTCACAAAT | CCATTGACAA | CATTGTAATC | TTGAGTGGCG | 720 |
| ATCAGCTTTA | TCGGATGAAT | TACATGGAAC | TTGTGCAGAA | ACATGTCGAG | GACGATGCTG | 780 |
| ATATCACTAT | ATCATGTGCT | CCTGTTGATG | AGAGCCGAGC | TTCTAAAAAT | GGGCTAGTGA | 840 |
| AGATTGATCA | TACTGGACGT | GTACTTCAAT | TCTTTGAAAA | ACCAAAGGGT | GCTGATTTGA | 900 |
| ATTCTATGAG | AGTTGAGACC | AACTTCCTGA | GCTATGCTAT | AGATGATGCA | CAGAAATATC | 960 |
| CATACCTTGC | ATCAATGGGC | ATTTATGTCT | TCAAGAAAGA | TGCACTTTTA | GACCTTCTCA | 1020 |
| AGTCAAAATA | TACTCAATTA | CATGACTTTG | GATCTGAAAT | CCTCCCAAGA | GCTGTACTAG | 1080 |
| ATCATAGTGT | GCAGGCATGC | ATTTTTACGG | GCTATTGGGA | GGATGTTGGA | ACAATCAAAT | 1140 |
| CATTCTTTGA | TGCAAACTTG | GCCCTCACTG | AGCAGCCTTC | CAAGTTTGAT | TTTTACGATC | 1200 |
| CAAAAACACC | TTTCTTCACT | GCACCCCGAT | GCTTGCCTCC | GACGCAATTG | GACAAGTGCA | 1260 |
| AGATGAAATA | TGCATTTATC | TCAGATGGTT | GCTTACTGAG | AGAATGCAAC | ATCGAGCATT | 1320 |
| CTGTGATTGG | AGTCTGCTCA | CGTGTCAGCT | CTGGATGTGA | ACTCAAGGAC | TCCGTGATGA | 1380 |
| TGGGAGCGGA | CATCTATGAA | ACTGAAGAAG | AAGCTTCAAA | GCTACTGTTA | GCTGGGAAGG | 1440 |
| TCCCGATTGG | AATAGGAAGG | AACACAAAGA | TAAGGAACTG | TATCATTGAC | ATGAATGCTA | 1500 |
| GGATTGGGAA | GAACGTGGTG | ATCACAAACA | GTAAGGGCAT | CCAAGAGGCT | GATCACCCGG | 1560 |
| AAGAAGGGTA | CTCGTACTAC | ATAAGGTCTG | GAATCGTGGT | GATCCTGAAG | AATGCAACCA | 1620 |
| TCAACGATGG | GTCTGTCATA | TAGATCGGCT | GCGTTTGCGT | CTACAAAACA | AGAACCTACA | 1680 |
| ATGGTATTGC | ATCGATGGAT | CGTGTAACCT | TGGTATGGTA | AGAGCCGCTT | GACAGGAAGT | 1740 |
| CGAGCTTCGG | GCGAAGATGC | TAGTCTGGCA | TGCTGTTCCT | TGACCATTTG | TGCTGCTAGT | 1800 |
| ATGTACCTGT | TATAAGCTGC | CCTAGAAGTT | GCAGCAAACC | TTTTTATGAA | CCTTTGTATT | 1860 |
| TCCATTACCC | TGCTTTGGAT | CAACTATATC | TGTCAGTCCT | ATATATTACT | AAATTTTTA | 1919 |

( 2 ) INFORMATION FOR SEQ ID NO:3:

( i ) SEQUENCE CHARACTERISTICS:
    ( A ) LENGTH: 518 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:3:

```
Met Gln Phe Ala Leu Ala Leu Asp Thr Asn Ser Gly Pro His Gln Ile
 1               5                  10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80
```

| | | | | | | | | | | | | | | |
|---|---|---|---|---|---|---|---|---|---|---|---|---|---|---|
| Ala | Asn | Arg | Val | Ser | Ala | Ile | Ile | Leu | Gly | Gly | Thr | Gly | Ser | Gln |
| | | | | 85 | | | | 90 | | | | | | 95 |
| Leu | Phe | Pro | Leu | Thr | Ser | Thr | Arg | Ala | Thr | Pro | Ala | Val | Pro | Val | Gly |
| | | | 100 | | | | | 105 | | | | 110 | | | |
| Gly | Cys | Tyr | Arg | Leu | Ile | Asp | Ile | Pro | Met | Ser | Asn | Cys | Phe | Asn | Ser |
| | | | 115 | | | | 120 | | | | | 125 | | | |
| Gly | Ile | Asn | Lys | Ile | Phe | Val | Met | Ser | Gln | Phe | Asn | Ser | Thr | Ser | Leu |
| | | 130 | | | | | 135 | | | | | 140 | | | |
| Asn | Arg | His | Ile | His | Arg | Thr | Tyr | Leu | Glu | Gly | Gly | Ile | Asn | Phe | Ala |
| 145 | | | | | 150 | | | | | 155 | | | | | 160 |
| Asp | Gly | Ser | Val | Gln | Val | Leu | Ala | Ala | Thr | Gln | Met | Pro | Glu | Glu | Pro |
| | | | | 165 | | | | | 170 | | | | | 175 | |
| Ala | Gly | Trp | Phe | Gln | Gly | Thr | Ala | Asp | Ser | Ile | Arg | Lys | Phe | Ile | Trp |
| | | | 180 | | | | | 185 | | | | | 190 | | |
| Val | Leu | Glu | Asp | Tyr | Tyr | Ser | His | Lys | Ser | Ile | Asp | Asn | Ile | Val | Ile |
| | | | 195 | | | | | 200 | | | | | 205 | | |
| Leu | Ser | Gly | Asp | Gln | Leu | Tyr | Arg | Met | Asn | Tyr | Met | Glu | Leu | Val | Gln |
| | | 210 | | | | | 215 | | | | | 220 | | | |
| Lys | His | Val | Glu | Asp | Ala | Asp | Ile | Thr | Ile | Ser | Cys | Ala | Pro | Val |
| 225 | | | | | 230 | | | | | 235 | | | | | 240 |
| Asp | Glu | Ser | Arg | Ala | Ser | Lys | Asn | Gly | Leu | Val | Lys | Ile | Asp | His | Thr |
| | | | | 245 | | | | | 250 | | | | | 255 | |
| Gly | Arg | Val | Leu | Gln | Phe | Phe | Glu | Lys | Pro | Lys | Gly | Ala | Asp | Leu | Asn |
| | | | | 260 | | | | | 265 | | | | | 270 | |
| Ser | Met | Arg | Val | Glu | Thr | Asn | Phe | Leu | Ser | Tyr | Ala | Ile | Asp | Asp | Ala |
| | | | 275 | | | | | 280 | | | | | 285 | | |
| Gln | Lys | Tyr | Pro | Tyr | Leu | Ala | Ser | Met | Gly | Ile | Tyr | Val | Phe | Lys | Lys |
| | | | 290 | | | | | 295 | | | | | 300 | | |
| Asp | Ala | Leu | Leu | Asp | Leu | Leu | Lys | Ser | Lys | Tyr | Thr | Gln | Leu | His | Asp |
| 305 | | | | | 310 | | | | | 315 | | | | | 320 |
| Phe | Gly | Ser | Glu | Ile | Leu | Pro | Arg | Ala | Val | Leu | Asp | His | Ser | Val | Gln |
| | | | | 325 | | | | | 330 | | | | | 335 | |
| Ala | Cys | Ile | Phe | Thr | Gly | Tyr | Trp | Glu | Asp | Val | Gly | Thr | Ile | Lys | Ser |
| | | | 340 | | | | | 345 | | | | | 350 | | |
| Phe | Phe | Asp | Ala | Asn | Leu | Ala | Leu | Thr | Glu | Gln | Pro | Ser | Lys | Phe | Asp |
| | | 355 | | | | | 360 | | | | | 365 | | | |
| Phe | Tyr | Asp | Pro | Lys | Thr | Pro | Phe | Phe | Thr | Ala | Pro | Arg | Cys | Leu | Pro |
| | 370 | | | | | 375 | | | | | 380 | | | | |
| Pro | Thr | Gln | Leu | Asp | Lys | Cys | Lys | Met | Lys | Tyr | Ala | Phe | Ile | Ser | Asp |
| 385 | | | | | 390 | | | | | 395 | | | | | 400 |
| Gly | Cys | Leu | Leu | Arg | Glu | Cys | Asn | Ile | Glu | His | Ser | Val | Ile | Gly | Val |
| | | | | 405 | | | | | 410 | | | | | 415 | |
| Cys | Ser | Arg | Val | Ser | Ser | Gly | Cys | Glu | Leu | Lys | Asp | Ser | Val | Met | Met |
| | | | 420 | | | | | 425 | | | | | 430 | | |
| Gly | Ala | Asp | Ile | Tyr | Glu | Thr | Glu | Glu | Ala | Ser | Lys | Leu | Leu | Leu |
| | | 435 | | | | | 440 | | | | | 445 | | | |
| Ala | Gly | Lys | Val | Pro | Ile | Gly | Ile | Gly | Arg | Asn | Thr | Lys | Ile | Arg | Asn |
| | | 450 | | | | | 455 | | | | | 460 | | | |
| Cys | Ile | Ile | Asp | Met | Asn | Ala | Arg | Ile | Gly | Lys | Asn | Val | Val | Ile | Thr |
| 465 | | | | | 470 | | | | | 475 | | | | | 480 |
| Asn | Ser | Lys | Gly | Ile | Gln | Glu | Ala | Asp | His | Pro | Glu | Glu | Gly | Tyr | Ser |
| | | | | 485 | | | | | 490 | | | | | 495 | |
| Tyr | Tyr | Ile | Arg | Ser | Gly | Ile | Val | Val | Ile | Leu | Lys | Asn | Ala | Thr | Ile |
| | | | 500 | | | | | 505 | | | | | 510 | | |

```
                Asn  Asp  Gly  Ser  Val  Ile
                          515
```

( 2 ) INFORMATION FOR SEQ ID NO:4:

( i ) SEQUENCE CHARACTERISTICS:
        ( A ) LENGTH: 1551 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
ATGCAGTTTG  CACTTGCATT  GGACACGAAC  TCAGGTCCTC  ACCAGATAAG  ATCTTGTGAG      60
GGTGATGGGA  TTGACAGGTT  GGAAAAATTA  AGTATTGGGG  GCAGAAAGCA  GGAGAAAGCT     120
TTGAGAAATA  GGTGCTTTGG  TGGTAGAGTT  GCTGCAACTA  CACAATGTAT  TCTTACCTCA     180
GATGCTTGTC  CTGAAACTCT  TCATTCTCAA  ACACAGTCCT  CTAGGAAAAA  TTATGCTGAT     240
GCAAACCGTG  TATCTGCGAT  CATTTTGGGC  GGAGGCACTG  GATCTCAGCT  CTTTCCTCTG     300
ACAAGCACAA  GAGCTACGCC  TGCTGTACCT  GTTGGAGGAT  GTTACAGGCT  TATTGATATC     360
CCTATGAGTA  ACTGCTTCAA  CAGTGGTATA  AATAAGATAT  TTGTGATGAG  TCAGTTCAAT     420
TCTACTTCGC  TTAACCGCCA  TATTCATCGT  ACATACCTTG  AAGGCGGGAT  CAACTTTGCT     480
GATGGATCTG  TACAGGTATT  AGCGGCTACA  CAAATGCCTG  AAGAGCCAGC  TGGATGGTTC     540
CAGGGTACAG  CAGACTCTAT  CAGAAAATTT  ATCTGGGTAC  TCGAGGATTA  TTACAGTCAC     600
AAATCCATTG  ACAACATTGT  AATCTTGAGT  GGCGATCAGC  TTTATCGGAT  GAATTACATG     660
GAACTTGTGC  AGAAACATGT  CGAGGACGAT  GCTGATATCA  CTATATCATG  TGCTCCTGTT     720
GATGAGAGCC  GAGCTTCTAA  AAATGGGCTA  GTGAAGATTG  ATCATACTGG  ACGTGTACTT     780
CAATTCTTTG  AAAAACCAAA  GGGTGCTGAT  TTGAATTCTA  TGAGAGTTGA  GACCAACTTC     840
CTGAGCTATG  CTATAGATGA  TGCACAGAAA  TATCCATACC  TTGCATCAAT  GGGCATTTAT     900
GTCTTCAAGA  AAGATGCACT  TTTAGACCTT  CTCAAGTCAA  AATATACTCA  ATTACATGAC     960
TTTGGATCTG  AAATCCTCCC  AAGAGCTGTA  CTAGATCATA  GTGTGCAGGC  ATGCATTTTT    1020
ACGGGCTATT  GGGAGGATGT  TGGAACAATC  AAATCATTCT  TTGATGCAAA  CTTGGCCCTC    1080
ACTGAGCAGC  CTTCCAAGTT  TGATTTTTAC  GATCCAAAAA  CACCTTTCTT  CACTGCACCC    1140
CGATGCTTGC  CTCCGACGCA  ATTGGACAAG  TGCAAGATGA  AATATGCATT  TATCTCAGAT    1200
GGTTGCTTAC  TGAGAGAATG  CAACATCGAG  CATTCTGTGA  TTGGAGTCTG  CTCACGTGTC    1260
AGCTCTGGAT  GTGAACTCAA  GGACTCCGTG  ATGATGGGAG  CGGACATCTA  TGAAACTGAA    1320
GAAGAAGCTT  CAAAGCTACT  GTTAGCTGGG  AAGGTCCCGA  TTGGAATAGG  AAGGAACACA    1380
AAGATAAGGA  ACTGTATCAT  TGACATGAAT  GCTAGGATTG  GAAGAACGT   GGTGATCACA    1440
AACAGTAAGG  GCATCCAAGA  GGCTGATCAC  CCGGAAGAAG  GGTCCTACTA  CATAAGGTCT    1500
GGAATCGTGG  TGATCCTGAA  GAATGCAACC  ATCAACGATG  GGTCTGTCAT  A            1551
```

( 2 ) INFORMATION FOR SEQ ID NO:5:

( i ) SEQUENCE CHARACTERISTICS:
        ( A ) LENGTH: 517 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

| Met | Gln | Phe | Ala | Leu | Ala | Leu | Asp | Thr | Asn | Ser | Gly | Pro | His | Gln | Ile |
| 1 | | | | 5 | | | | | 10 | | | | | 15 | |

| Arg | Ser | Cys | Glu | Gly | Asp | Gly | Ile | Asp | Arg | Leu | Glu | Lys | Leu | Ser | Ile |
| | | | 20 | | | | 25 | | | | | 30 | | | |

| Gly | Gly | Arg | Lys | Gln | Glu | Lys | Ala | Leu | Arg | Asn | Arg | Cys | Phe | Gly | Gly |
| | | 35 | | | | | 40 | | | | | 45 | | | |

| Arg | Val | Ala | Ala | Thr | Thr | Gln | Cys | Ile | Leu | Thr | Ser | Asp | Ala | Cys | Pro |
| | 50 | | | | 55 | | | | | 60 | | | | | |

| Glu | Thr | Leu | His | Ser | Gln | Thr | Gln | Ser | Ser | Arg | Lys | Asn | Tyr | Ala | Asp |
| 65 | | | | | 70 | | | | | 75 | | | | | 80 |

| Ala | Asn | Arg | Val | Ser | Ala | Ile | Ile | Leu | Gly | Gly | Gly | Thr | Gly | Ser | Gln |
| | | | | 85 | | | | | 90 | | | | | 95 | |

| Leu | Phe | Pro | Leu | Thr | Ser | Thr | Arg | Ala | Thr | Pro | Ala | Val | Pro | Val | Gly |
| | | | 100 | | | | | 105 | | | | | 110 | | |

| Gly | Cys | Tyr | Arg | Leu | Ile | Asp | Ile | Pro | Met | Ser | Asn | Cys | Phe | Asn | Ser |
| | | | 115 | | | | 120 | | | | | 125 | | | |

| Gly | Ile | Asn | Lys | Ile | Phe | Val | Met | Ser | Gln | Phe | Asn | Ser | Thr | Ser | Leu |
| | | | 130 | | | | 135 | | | | | 140 | | | |

| Asn | Arg | His | Ile | His | Arg | Thr | Tyr | Leu | Glu | Gly | Gly | Ile | Asn | Phe | Ala |
| 145 | | | | | 150 | | | | | 155 | | | | | 160 |

| Asp | Gly | Ser | Val | Gln | Val | Leu | Ala | Ala | Thr | Gln | Met | Pro | Glu | Glu | Pro |
| | | | | 165 | | | | | 170 | | | | | 175 | |

| Ala | Gly | Trp | Phe | Gln | Gly | Thr | Ala | Asp | Ser | Ile | Arg | Lys | Phe | Ile | Trp |
| | | | 180 | | | | | 185 | | | | | 190 | | |

| Val | Leu | Glu | Asp | Tyr | Tyr | Ser | His | Lys | Ser | Ile | Asp | Asn | Ile | Val | Ile |
| | | 195 | | | | | 200 | | | | | 205 | | | |

| Leu | Ser | Gly | Asp | Gln | Leu | Tyr | Arg | Met | Asn | Tyr | Met | Glu | Leu | Val | Gln |
| | 210 | | | | | 215 | | | | | 220 | | | | |

| Lys | His | Val | Glu | Asp | Asp | Ala | Asp | Ile | Thr | Ile | Ser | Cys | Ala | Pro | Val |
| 225 | | | | 230 | | | | | 235 | | | | | | 240 |

| Asp | Glu | Ser | Arg | Ala | Ser | Lys | Asn | Gly | Leu | Val | Lys | Ile | Asp | His | Thr |
| | | | | 245 | | | | | 250 | | | | | 255 | |

| Gly | Arg | Val | Leu | Gln | Phe | Phe | Glu | Lys | Pro | Lys | Gly | Ala | Asp | Leu | Asn |
| | | | 260 | | | | | 265 | | | | | 270 | | |

| Ser | Met | Arg | Val | Glu | Thr | Asn | Phe | Leu | Ser | Tyr | Ala | Ile | Asp | Asp | Ala |
| | | 275 | | | | | 280 | | | | | 285 | | | |

| Gln | Lys | Tyr | Pro | Tyr | Leu | Ala | Ser | Met | Gly | Ile | Tyr | Val | Phe | Lys | Lys |
| | 290 | | | | | 295 | | | | | 300 | | | | |

| Asp | Ala | Leu | Leu | Asp | Leu | Leu | Lys | Ser | Lys | Tyr | Thr | Gln | Leu | His | Asp |
| 305 | | | | | 310 | | | | | 315 | | | | | 320 |

| Phe | Gly | Ser | Glu | Ile | Leu | Pro | Arg | Ala | Val | Leu | Asp | His | Ser | Val | Gln |
| | | | | 325 | | | | | 330 | | | | | 335 | |

| Ala | Cys | Ile | Phe | Thr | Gly | Tyr | Trp | Glu | Asp | Val | Gly | Thr | Ile | Lys | Ser |
| | | | 340 | | | | | 345 | | | | | 350 | | |

| Phe | Phe | Asp | Ala | Asn | Leu | Ala | Leu | Thr | Glu | Gln | Pro | Ser | Lys | Phe | Asp |
| | | 355 | | | | | 360 | | | | | 365 | | | |

| Phe | Tyr | Asp | Pro | Lys | Thr | Pro | Phe | Phe | Thr | Ala | Pro | Arg | Cys | Leu | Pro |
| | 370 | | | | | 375 | | | | | 380 | | | | |

| Pro | Thr | Gln | Leu | Asp | Lys | Cys | Lys | Met | Lys | Tyr | Ala | Phe | Ile | Ser | Asp |
| 385 | | | | | 390 | | | | | 395 | | | | | 400 |

| Gly | Cys | Leu | Leu | Arg | Glu | Cys | Asn | Ile | Glu | His | Ser | Val | Ile | Gly | Val |
| | | | | 405 | | | | | 410 | | | | | 415 | |

-continued

| | | | | | | | | | | | | | | |
|---|---|---|---|---|---|---|---|---|---|---|---|---|---|---|
| Cys | Ser | Arg | Val 420 | Ser | Ser | Gly | Cys | Glu 425 | Leu | Lys | Asp | Ser | Val 430 | Met | Met |
| Gly | Ala | Asp 435 | Ile | Tyr | Glu | Thr | Glu 440 | Glu | Glu | Ala | Ser | Lys 445 | Leu | Leu | Leu |
| Ala | Gly 450 | Lys | Val | Pro | Ile | Gly 455 | Ile | Gly | Arg | Asn | Thr 460 | Lys | Ile | Arg | Asn |
| Cys 465 | Ile | Ile | Asp | Met | Asn 470 | Ala | Arg | Ile | Gly | Lys 475 | Asn | Val | Val | Ile | Thr 480 |
| Asn | Ser | Lys | Gly | Ile 485 | Gln | Glu | Ala | Asp | His 490 | Pro | Glu | Glu | Gly | Ser 495 | Tyr |
| Tyr | Ile | Arg | Ser 500 | Gly | Ile | Val | Val | Ile 505 | Leu | Lys | Asn | Ala | Thr 510 | Ile | Asn |
| Asp | Gly | Ser 515 | Val | Ile | | | | | | | | | | | |

MATERIALS AND METHODS FOR INCREASING CORN SEED WEIGHT

CROSS-REFERENCE TO A RELATED APPLICATION

This is a division of application Ser. No. 08/485,241, filed Jun. 7, 1995, now U.S. Pat. No. 5,650,557, which is a continuation-in-part of application Ser. No. 08/299,675, filed Sep. 1, 1994, now U.S. Pat. No. 5,589,618.

This invention was made with government support under National Science Foundation grant number 93052818. The government has certain rights in this invention.

BACKGROUND OF THE INVENTION

ADP-glucose pyrophosphorylase (AGP) catalyzes the conversion of ATP and α-glucose-1-phosphate to ADP-glucose and pyrophosphate. ADP-glucose is used as a glycosyl donor in starch biosynthesis by plants and in glycogen biosynthesis by bacteria. The importance of ADP-glucose pyrophosphorylase as a key enzyme in the regulation of starch biosynthesis was noted in the study of starch deficient mutants of maize (Zea mays) endosperm (Tsai and Nelson, 1966; Dickinson and Preiss, 1969). AGP enzymes have been isolated from both bacteria and plants. Bacterial AGP consists of a homotetramer, while plant AGP from photosynthetic and non-photosynthetic tissues is a heterotetramer composed of two different subunits. The plant enzyme is encoded by two different genes, with one subunit being larger than the other. This feature has been noted in a number of plants. The AGP subunits in spinach leaf have molecular weights of 54 kDa and 51 kDa, as estimated by SDS-PAGE. Both subunits are immunoreactive with antibody raised against purified AGP from spinach leaves (Copeland and Preiss, 1981; Morell et al., 1987). Immunological analysis using antiserum prepared against the small and large subunits of spinach leaf showed that potato tuber AGP is also encoded by two genes (Okita et al., 1990). The cDNA clones of the two subunits of potato tuber (50 and 51 kDa) have also been isolated and sequenced (Muller-Rober et al., 1990; Nakata et al., 1991).

As Hannah and Nelson (Hannah and Nelson, 1975 and 1976) postulated, both Shrunken-2 (Sh2) (Bhave et al., 1990) and Brittle-2 (Bt2) (Bae et al., 1990) are structural genes of maize endosperm ADP-glucose pyrophosphorylase. Sh2 and Bt2 encode the large subunit and small subunit of the enzyme, respectively. From cDNA sequencing, Sh2 and Bt2 proteins have predicted molecular weight of 57,179 Da (Shaw and Hannah, 1992) and 52,224 Da, respectively. The endosperm is the site of most starch deposition during kernel development in maize. Sh2 and bt2 maize endosperm mutants have greatly reduced starch levels corresponding to deficient levels of AGP activity. Mutations of either gene have been shown to reduce AGP activity by about 95% (Tsai and Nelson, 1966; Dickinson and Preiss, 1969). Furthermore, it has been observed that enzymatic activities increase with the dosage of functional wild type Sh2 and Bt2 alleles, whereas mutant enzymes have altered kinetic properties. AGP is the rate limiting step in starch biosynthesis in plants. Stark et al. placed a mutant form of E. coli AGP in potato tuber and obtained a 35% increase in starch content (Stark, 1992).

The cloning and characterization of the genes encoding the AGP enzyme subunits have been reported for various plants. These include Sh2 cDNA (Bhave et al., 1990), Sh2 genomic DNA (Shaw and Hannah, 1992), and Bt2 cDNA (Bae et al., 1990) from maize; small subunit cDNA (Anderson et al., 1989) and genomic DNA (Anderson et al., 1991) from rice; and small and large subunit cDNAs from spinach leaf (Morell et al., 1987) and potato tuber (Muller-Rober et al., 1990; Nakata et al., 1991). In addition, cDNA clones have been isolated from wheat endosperm and leaf tissue (Olive et al., 1989) and Arabidopsis thaliana leaf (Lin et al., 1988).

AGP functions as an allosteric enzyme in all tissues and organisms investigated to date. The allosteric properties of AGP were first shown to be important in E. coli. A glycogen-overproducing E. coli mutant was isolated and the mutation mapped to the structural gene for AGP, designated as glyC. The mutant E. coli, known as glyC-16, was shown to be more sensitive to the activator, fructose 1,6 bisphosphate, and less sensitive to the inhibitor, cAMP (Preiss, 1984). Although plant AGP's are also allosteric, they respond to different effector molecules than bacterial AGP's. In plants, 3-phosphoglyceric acid (3-PGA) functions as an activator while phosphate ($PO_4$) serves as an inhibitor (Dickinson and Preiss, 1969).

In view of the fact that endosperm starch content comprises approximately 70% of the dry weight of the seed, alterations in starch biosynthesis correlate with seed weight. Unfortunately, the undesirable effect associated with such alterations has been an increase in the relative starch content of the seed. Therefore, the development of a method for increasing seed weight in plants without increasing the relative starch content of the seed is an object of the subject invention.

BRIEF SUMMARY OF THE INVENTION

The subject invention concerns a novel variant of the Shrunken-2 (Sh2) gene from maize. The Sh2 gene encodes ADP-glucose pyrophosphorylase (AGP), an important enzyme involved in starch synthesis in the major part of the corn seed, the endosperm. In a preferred embodiment, the novel gene of the subject invention encodes a variant AGP protein which has two additional amino acids inserted into the sequence. The variant gene described herein has been termed the Sh2-m1Rev6 gene. Surprisingly, the presence of the Sh2-m1Rev6 gene in a corn plant results in a substantial increase in corn seed weight when compared to wild type seed weight, but does so in the absence of an increase in the relative starch content of the kernel.

The subject invention further concerns a method of using the variant sh2 gene in maize to increase seed weight. The subject invention also concerns plants having the variant sh2 gene and expressing the mutant protein in the seed endosperm.

As described herein, the sh2 variant, Sh2-m1Rev6, can be produced using in vivo, site-specific mutagenesis. A transposable element was used to create a series of mutations in the sequence of the gene that encodes the enzyme. As a result, the Sh2-m1Rev6 gene encodes an additional amino acid pair within or close to the allosteric binding site of the protein.

BRIEF DESCRIPTION OF THE SEQUENCES

SEQ ID NO. 1 is the genomic nucleotide sequence of the Sh2-m1Rev6 gene.

SEQ ID NO. 2 is the nucleotide sequence of the Sh2-m1Rev6 cDNA.

SEQ ID NO. 3 is the amino acid sequence of the protein encoded by nucleotides 87 through 1640 of SEQ ID NO. 2.

SEQ ID NO. 4 is a nucleotide sequence encoding the amino acid sequence shown in SEQ ID NO. 5.

SEQ ID NO. 5 is the amino acid sequence of an ADP-glucose pyrophosphorylase (AGP) enzyme subunit containing a single serine insertion.

DETAILED DISCLOSURE OF THE INVENTION

The subject invention provides novel variants of the Shrunken-2 (Sh2) gene and a method for increasing seed weight in a plant through the expression of the variant sh2 gene. The Sh2 gene encodes a subunit of the enzyme ADP-glucose pyrophosphorylase (AGP) in maize endosperm. One variant gene, denoted herein as Sh2-m1Rev6, contains an insertion mutation that encodes an additional tyrosine:serine or serine:tyrosine amino acid pair that is not present in the wild type protein. The sequences of the wild type DNA and protein are disclosed in Shaw and Hannah, 1992. The in vivo, site-specific mutation which resulted in the tyrosine:serine or serine:tyrosine insertion, was generated in Sh2 using the transposable element, dissociation (Ds), which can insert into, and be excised from, the Sh2 gene under appropriate conditions. Ds excision can alter gene expression through the addition of nucleotides to a gene at the site of excision of the element.

In a preferred embodiment, insertion mutations in the Sh2 gene were obtained by screening for germinal revertants after excision of the Ds transposon from the gene. The revertants were generated by self-pollination of a stock containing the Ds-Sh2 mutant allele, the Activator (Ac) element of this transposable element system, and appropriate outside markers. The Ds element can transpose when the Ac element is present. Wild type seed were selected, planted, self-pollinated and crossed onto a tester stock. Results from this test cross were used to remove wild type alleles due to pollen contamination. Seeds homozygous for each revertant allele were obtained from the self-progeny. Forty-four germinal revertants of the Ds-induced sh2 mutant were collected.

Cloning and sequencing of the Ds insertion site showed that the nucleotide insertion resides in the area of the gene that encodes the binding site for the AGP activator, 3-PGA (Morrell, 1988). Of the 44 germinal revertants obtained, 28 were sequenced. The sequenced revertants defined 5 isoalleles of sh2: 13 restored the wild type sequence, 11 resulted in the insertion of the amino acid tyrosine, two contained an additional serine (inserted between amino acid residues 494 and 495, respectively, of the native protein sequence), one revertant contained a two amino acid insertion, tyrosine:tyrosine, and the last one, designated as Sh2-m1Rev6, contained the two amino acid insertion, tyrosine:serine or serine:tyrosine. The Sh2-m1Rev6 variant encodes an AGP enzyme subunit that has either the tyrosine:serine amino acid pair inserted between the glycine and tyrosine at amino acid residues 494 and 495, respectively, of the native protein, or the serine:tyrosine amino acid pair inserted between the two tyrosine residues located at position 495 and 496 of the native protein sequence. Due to the sequence of the amino acids in the area of the insertions, the Sh2-m1Rev6 variant amino acid sequences encoded by each of these insertions are identical to each other.

Surprisingly, the expression of the Sh2-m1Rev6 gene in maize resulted in a significant increase in seed weight over that obtained from maize expressing the wild-type Sh2 allele. Moreover, seeds from plants having the Sh2-m1Rev6 gene contained approximately the same percentage starch content relative to any of the other revertants generated. In a preferred embodiment, the Sh2-m1Rev6 gene is contained in homozygous form within the genome of a plant seed.

The subject invention further concerns a plant that has the Sh2-m1Rev6 gene incorporated into its genome. Other alleles disclosed herein can also be incorporated into a plant genome. In a preferred embodiment, the plant is a monocotyledonous species. More preferably, the plant may be *Zea mays*. Plants having the Sh2-m1Rev6 gene can be grown from seeds that have the gene in their genome. In addition, techniques for transforming plants with a gene are known in the art.

Because of the degeneracy of the genetic code, a variety of different polynucleotide sequences can encode the variant AGP polypeptide disclosed herein. In addition, it is well within the skill of a person trained in the art to create alternative polynucleotide sequences encoding the same, or essentially the same, polypeptide of the subject invention. These variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by Sh2-m1Rev6 or the other alleles. The subject invention also contemplates those polynucleotide molecules having sequences which are sufficiently homologous with the wild type Sh2 DNA sequence so as to permit hybridization with that sequence under standard high-stringency conditions. Such hybridization conditions are conventional in the art (see, e.g., Maniatis et al., 1989).

The polynucleotide molecules of the subject invention can be used to transform plants to express the Sh2-m1Rev6 allele, or other alleles of the subject invention, in those plants. In addition, the polynucleotides of the subject invention can be used to express the recombinant variant AGP enzyme. They can also be used as a probe to detect related enzymes. The polynucleotides can also be used as DNA sizing standards.

The polypeptides encoded by the polynucleotides of the subject invention can be used to catalyze the conversion of ATP and α-glucose-1-phosphate to ADP-glucose and pyrophosphate, or to raise an immunogenic response to the AGP enzymes and variants thereof. They can also be used as molecular weight standards, or as an inert protein in an assay.

The following are examples which illustrate procedures and processes, including the best mode, for practicing the invention. These examples should not be construed as limiting, and are not intended to be a delineation of all possible modifications to the technique. All percentages are by weight and all solvent mixture proportions are by volume unless otherwise noted.

EXAMPLE 1

Expression of Sh2-m1Rev6 Gene in Maize Endosperm

Homozygous plants of each revertant obtained after excision of the Ds transposon were crossed onto the F1 hybrid corn, "Florida Stay Sweet." This sweet corn contains a null allele for the Sh2 gene, termed sh2-R. Resulting endosperms contained one dose of the functional allele from a revertant and two female-derived null alleles, denoted by the following genotype Sh2-m1RevX/sh2-R/sh2-R, where X represents one of the various isoalleles of the revertants. Crosses were made during two growing seasons.

Resulting seed weight data for each revertant and wild type seed are shown in Table 1. The first column shows the amino acid insertion in the AGP enzyme obtained after the in vivo, site-specific mutagenesis.

TABLE 1

| Sequence alteration | # of revertants | Average Seed weight | Standard deviation |
|---|---|---|---|
| wild type | 13 | 0.250 grams | 0.015 |
| tyrosine | 11 | 0.238 grams | 0.025 |
| serine | 2 | 0.261 grams | 0.014 |
| tyr, tyr | 1 | 0.223 grams | nd* |
| tyr, ser (Rev6) | 1 | 0.289 grams | 0.022 |

*nd = not determined

The data shown in Table 1 represents the average kernel seed weight for each revertant over the course of two growing seasons. The expression of the Sh2-m1Rev6 gene to produce the Rev6 mutant AGP subunit gave rise to an almost 16% increase in seed weight in comparison to the wild type revertant. The revertants having the single serine insertion also showed an increase in average seed weight over wild type seed weight.

In addition, starch content was determined on the kernels analyzed above using various methodologies. The analysis showed that Sh2-m1Rev6 containing kernels were no higher in percentage starch relative to kernels expressing the other alleles shown in the table above. Therefore, it appears that the increase in seed weight is not solely a function of starch content.

Corn seeds that contain at least one functional Sh2-m1Rev6 allele have been deposited with the American Type Culture Collection (ATCC), 12301 Parklawn Drive, Rockville, Md. 20852 USA, on May 16, 1996 and assigned accession number ATCC 97624.

The seeds have been deposited under conditions that assure that access to the culture will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject seed deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject seed deposit will be irrevocably removed upon the granting of a patent disclosing it.

As would be apparent to a person of ordinary skill in the art, seeds and plants that are homozygous for the Sh2-m1Rev6 allele can be readily prepared from heterozygous seeds using techniques that are standard in the art. In addition, the Sh2-m1Rev6 gene can be readily obtained from the deposited seeds.

The skilled artisan, using standard techniques known in the art, can also prepare polynucleotide molecules that encode additional amino acid residues, such as serine, at the location of the insertions in the subject revertants. Such polynucleotide molecules are included within the scope of the subject invention.

It should be understood that the examples and embodiments described herein are for illustrative purposes only and that various modifications or changes in light thereof will be suggested to persons skilled in the art and are to be included within the scope and purview of this application and the scope of the appended claims.

REFERENCES

Anderson, J. M., J. Hnilo, R. Larson, t. W. Okita, M. Morell, J. Preiss (1989) "The encoded primary sequence of a rice seed ADP-glucose pyrophosphorylase subunit and its homology to the bacterial enzyme," *J. Biol. Chem.* 264:12238–12242.

Anderson, J. M., R. Larson, D. Landencia, W. T. Kim, D. Morrow, T. W. Okita, J. Preiss (1991) "Molecular characterization of the gene encoding a rice endosperm-specific ADP-glucose pyrophosphorylase subunit and its developmental pattern of transcription," *Gene* 97:199–205.

Bae, J. M., M. Giroux, L. C. Hannah (1990) "Cloning and characterization of the Brittle-2 gene of maize," *Maydica* 35:317–322.

Bhave, M. R., S. Lawrence, C. Barton, L. C. Hannah (1990) "Identification and molecular characterization of Shrunken-2 cDNA clones of maize," *Plant Cell* 2:581–588.

Copeland, L., J. Preiss (1981) "Purification of spinach leaf ADP-glucose pyrophosphorylase," *Plant Physiol.* 68:996–1001.

Dickinson, D. B., J. Preiss (1969) "Presence of ADP-glucose pyrophosphorylase in Shrunken-2 and Brittle-2 mutants of maize endosperm," *Plant Physiol.* 44:1058–1062.

Hannah, L. C., O. E. Nelson (1975) "Characterization of adenosine diphosphate glucose pyrophosphorylase from developing maize seeds," *Plant Physiol.* 55:297–302.

Hannah, L. C., O. E. Nelson (1976) "Characterization of adenosine diphosphate glucose pyrophosphorylase from Shrunken-2 and Brittle-2 mutants of maize," *Biochem. Genet.* 14:547–560.

Lin, T., T. Caspar, C. Somerville, J. Preiss (1988) "A starch deficient mutant of *Arabidopsis thaliana* with low ADP-glucose pyrophosphorylase activity lacks one of the two subunits of the enzyme," *Plant Physiol.* 88:1175–1181.

Maniatis, T., E. F. Fritsch, J. Sambrook (1989) *Molecular Cloning: A Laboratory Manual,* 2d Edition, Cold Spring Harbor Laboratory, Cold Spring Harbor, N.Y.

Morell, M., M. Bloon, V. Knowles, J. Preiss (1988) "Subunit structure of spinach leaf ADP-glucose pyrophosphorylase," *J. Bio. Chem.* 263:633.

Muller-Rober, B. T., J. Kossmann, L. C. Hannah, L. Willmitzer, U. Sounewald (1990) "One of the two different ADP-glucose pyrophosphorylase genes from potato responds strongly to elevated levels of sucrose," *Mol. Gen. Genet.* 224:136–146.

Nakata, P. A., T. W. Greene, J. M. Anderson, B. J. Smith-White, T. W. Okita, J. Preiss (1991) "Comparison of primary sequences of two potato tuber ADP-glucose pyrophosphorylase subunits," *Plant Mol. Biol.* 17:1089–1093.

Okita, T. W., P. A. Nakata, J. M. Anderson, J. Sowokinos, M. Morell, J. Preiss (1990) "The subunit structure of potato tuber ADP-glucose pyrophosphorylase," *Plant Physiol.* 93:785–790.

Olive, M. R., R. J. Ellis, W. W. Schuch (1989) "Isolation and nucleotide sequences of cDNA clones encoding ADP-glucose pyrophosphorylase polypeptides from wheat leaf and endoosperm," *Plant Physiol. Mol. Biol.* 12:525–538.

Preiss, J. (1984) "Bacterial glycogen synthesis and it regulation," *Ann. Rev. Microbiol.* 419–458.

Shaw, J. R., L. C. Hannah (1992) "Genomic nucleotide sequence of a wild type Shrunken-2 allele of *Zea mays*," *Plant Physiol.* 98:1214–1216.

Starke, et al. (1992) "Regulation of the amount of starch in plant tissues by ADP-glucose pyrophosphorylase," *Science* 258:287.

Tsai, C., O. E. Nelson (1966) "Starch-deficient maize mutant lacking adenosine diphosphate glucose pyrophosphorylase activity," *Science* 151:341–343.

We claim:

1. A variant ADP-glucose pyrophosphorylase (AGP) protein, wherein said protein has at least one serine residue inserted between amino acids 494 and 495 of the wild type AGP protein sequence of corn.

2. The variant AGP protein, according to claim 1, wherein said protein has the amino acid pair tyrosine:serine inserted between amino acids 494 and 495 of the wild-type AGP protein sequence.

3. A variant ADP-glucose pyrophosphorylase (AGP) protein, wherein said protein has the amino acid pair serine:tyrosine inserted between amino acids 495 an 496 of the wild-type AGP protein sequence of corn.

4. The variant AGP protein, according to claim 1, wherein said protein consists of an amino acid sequence selected from the group consisting of SEQ ID NO. 5 and SEQ ID NO. 3.

5. The variant AGP protein, according to claim 1, wherein said protein is expressed in the endosperm of corn during seed development.

6. The variant AGP protein, according to claim 3, wherein said protein is expressed in the endosperm of corn during seed development.

* * * * *

UNITED STATES PATENT AND TRADEMARK OFFICE
CERTIFICATE OF CORRECTION

PATENT NO. : 5,872,216
DATED : February 16, 1999
INVENTOR(S) : L. Curtis Hannah, et. al.

It is certified that error appears in the above-identified patent and that said Letters Patent is hereby corrected as shown below:

Column 23, line 32: "495 an 496 of the wild type" should read --495 and 496 of the wild-type--.

Column 24: Please add the following:

--7. The variant AGP protein, according to claim 3, wherein said protein consists of an amino acid sequence identified as SEQ ID NO. 3.--

Signed and Sealed this

Twenty-fourth Day of August, 1999

Attest:

Q. TODD DICKINSON

*Attesting Officer*   *Acting Commissioner of Patents and Trademarks*